United States Patent [19]
Stone et al.

[11] Patent Number: 5,591,181
[45] Date of Patent: Jan. 7, 1997

[54] SURGICAL SUTURING APPARATUS WITH LOADING MECHANISM

[75] Inventors: Corbett W. Stone, Newtown, Conn.; Stephen W. Zlock, Hawthorne, N.Y.; David A. Nicholas, Trumbull, Conn.

[73] Assignee: United States Surgical Corporation, Norwalk, Conn.

[21] Appl. No.: 570,150

[22] Filed: Dec. 11, 1995

Related U.S. Application Data

[63] Continuation of Ser. No. 293,233, Aug. 19, 1994, Pat. No. 5,478,344, which is a continuation-in-part of Ser. No. 134,145, Oct. 8, 1993, abandoned.

[51] Int. Cl.$^6$ ..................................... A61B 17/04
[52] U.S. Cl. ................ 606/144; 206/63.3; 206/339; 206/340; 206/341
[58] Field of Search ................... 606/144, 139; 206/63.3, 339, 340, 341; 221/191

[56] References Cited

U.S. PATENT DOCUMENTS

| | | | |
|---|---|---|---|
| 3,901,244 | 8/1975 | Schweizer | 221/2 |
| 4,084,692 | 4/1978 | Bilweis | 206/403 |
| 4,116,333 | 9/1978 | Pavel | 206/380 |
| 4,135,623 | 1/1979 | Thyen | 206/63.3 |
| 4,183,431 | 1/1980 | Schmidt et al. | |
| 4,418,821 | 12/1983 | Sandel | |
| 4,424,898 | 1/1984 | Thyen et al. | |
| 4,449,630 | 5/1984 | Filhol | 206/369 |
| 4,496,045 | 1/1985 | Ferguson et al. | 206/476 |
| 4,524,891 | 6/1985 | Silva | 206/382 |
| 4,821,878 | 4/1989 | Jones | 206/370 |
| 5,056,658 | 10/1991 | Sobel et al. | 206/63.3 |
| 5,078,730 | 1/1992 | Li et al. | 606/228 |
| 5,086,914 | 2/1992 | Mish et al. | 206/63.3 |
| 5,226,536 | 7/1993 | Elliott | 206/369 |
| 5,271,495 | 12/1993 | Alpern | 206/63.3 |

FOREIGN PATENT DOCUMENTS 2260704  9/1991  United Kingdom.

*Primary Examiner*—Gary Jackson

[57] ABSTRACT

A surgical apparatus is provided for manipulating a surgical needle and an associated loading mechanism is provided for replacing the surgical needle. The surgical apparatus comprises an elongated body portion, first and second jaw elements extending from the body portion, securing means for securing the surgical needle, releasing means cooperating with the securing means for releasing the surgical needle and locking means cooperating with the securing means for preventing at least one of the jaw elements from moving. A loading mechanism is also provided and includes structure for supporting a surgical needle and a storage member for retaining at least a portion of a length of suture material attached to the surgical needle.

8 Claims, 17 Drawing Sheets

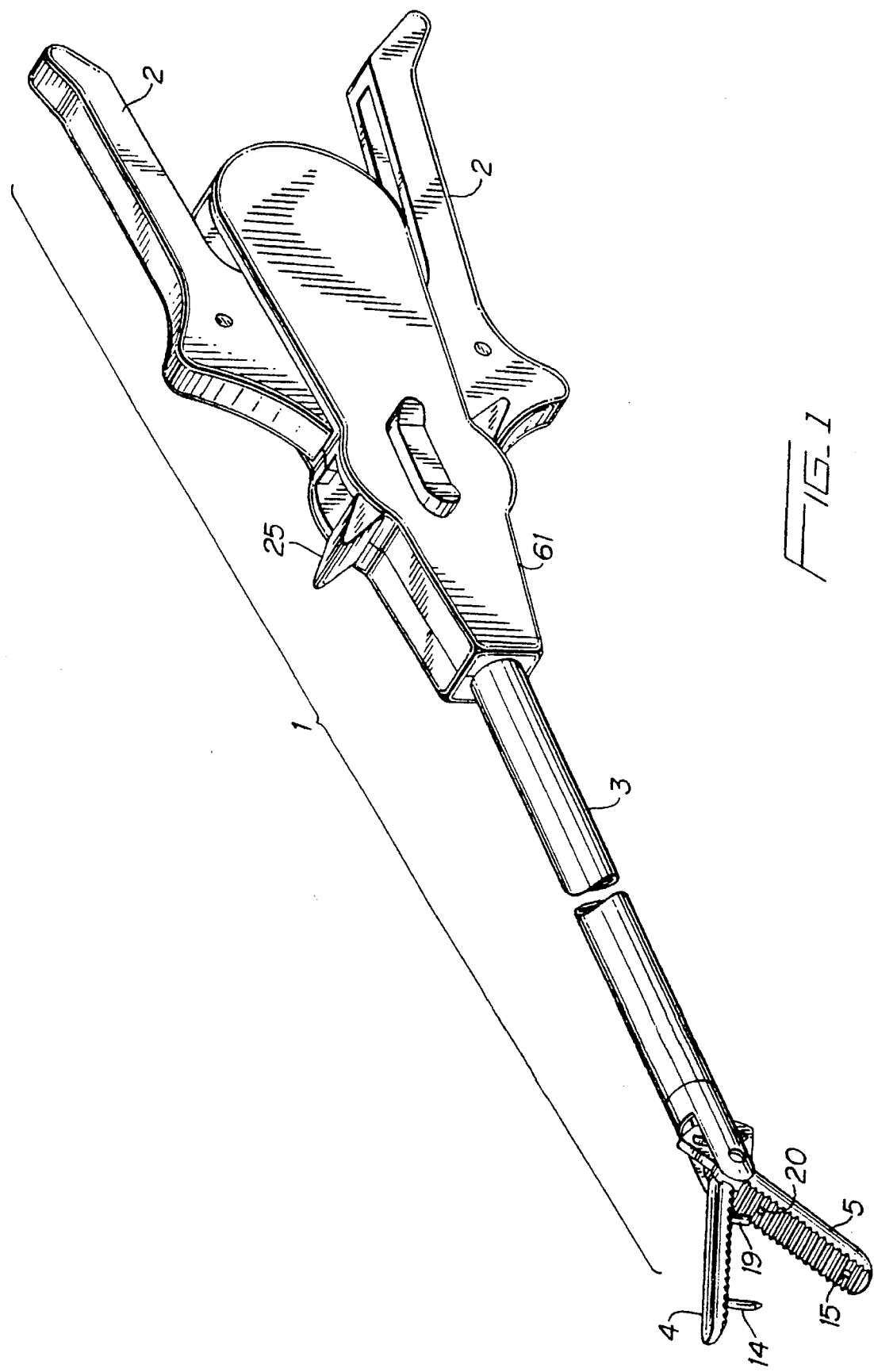

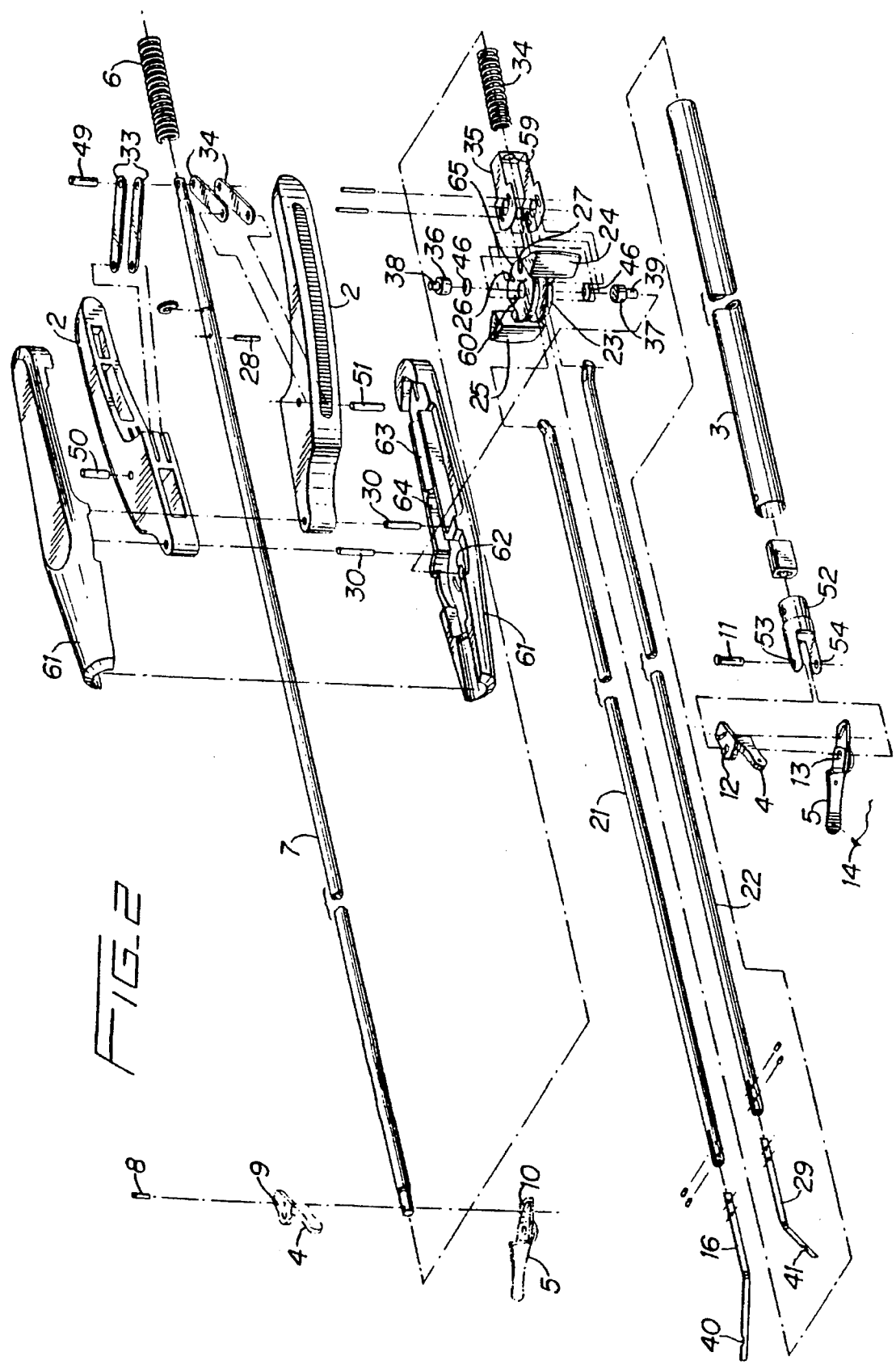

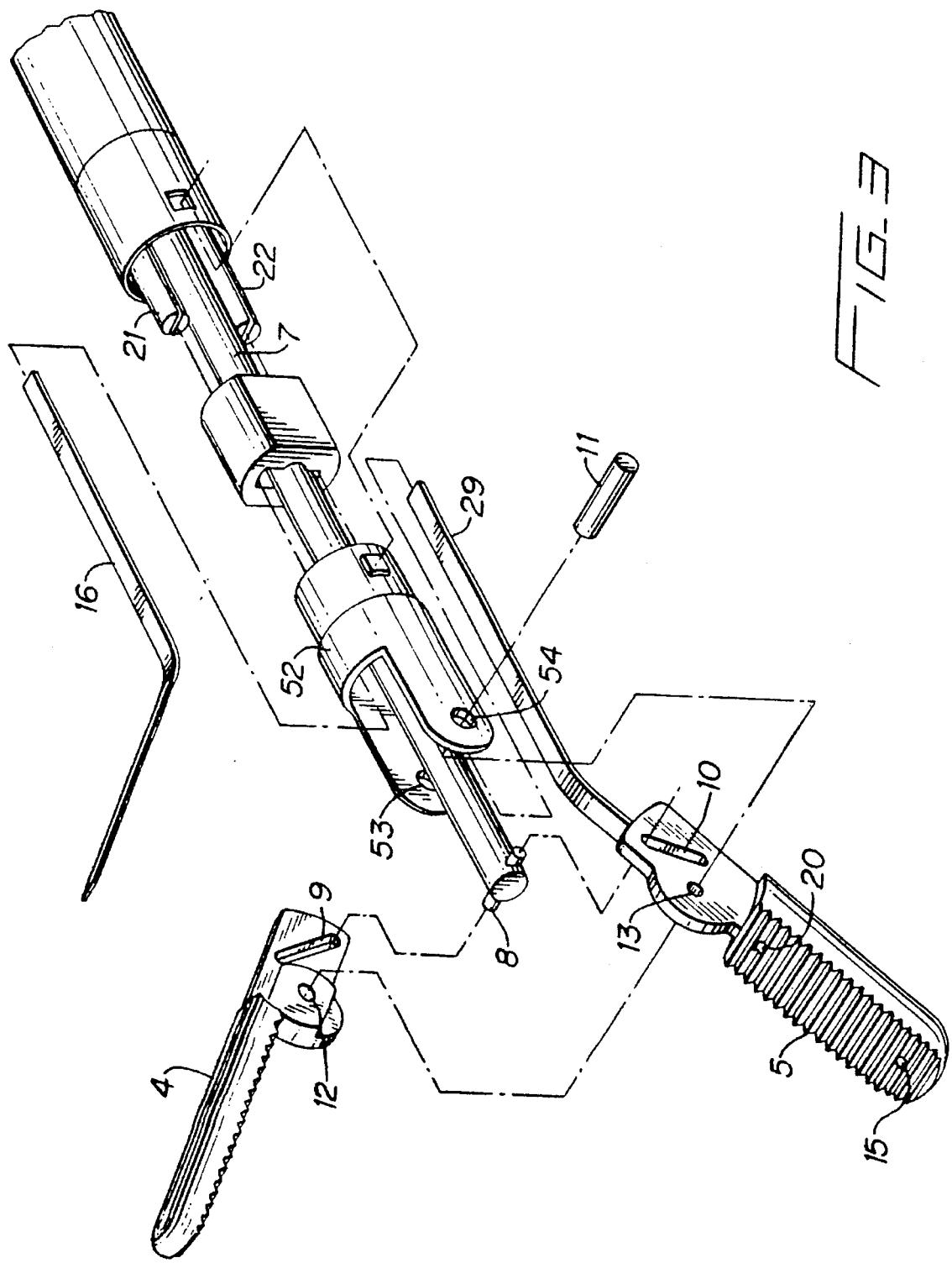

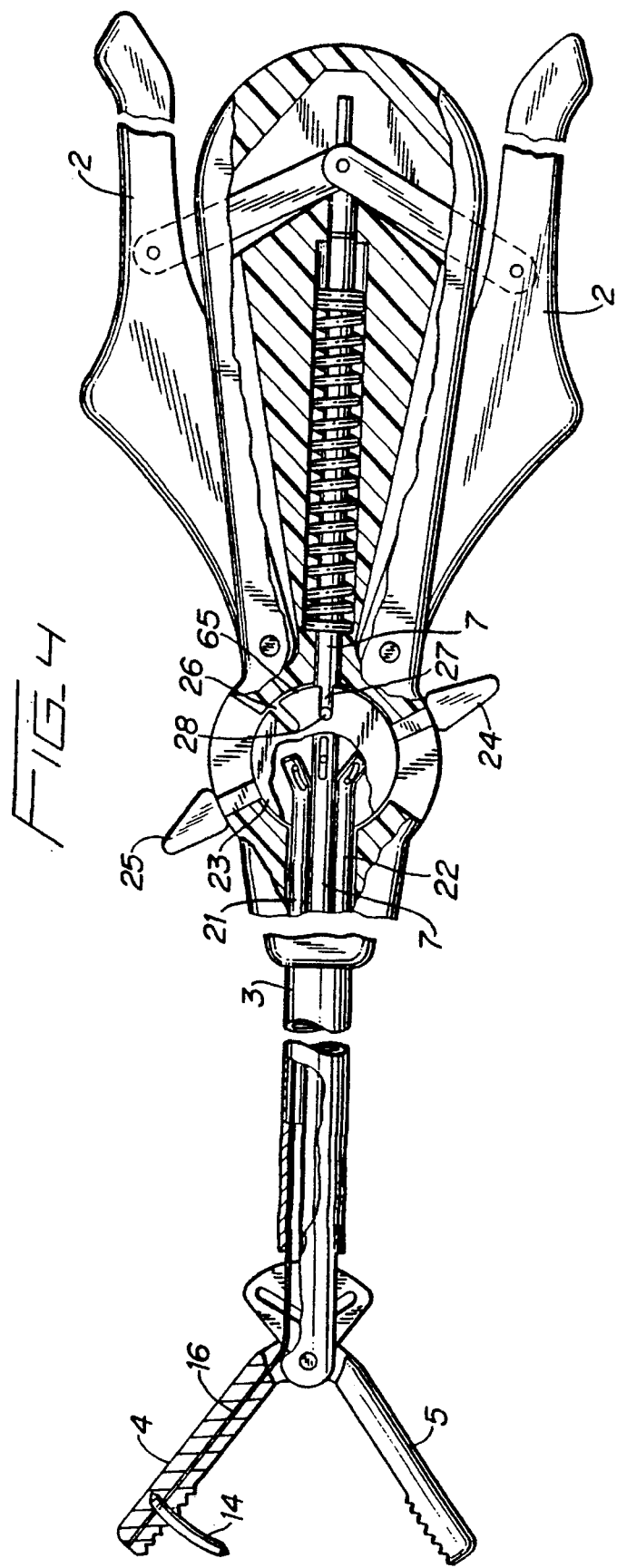

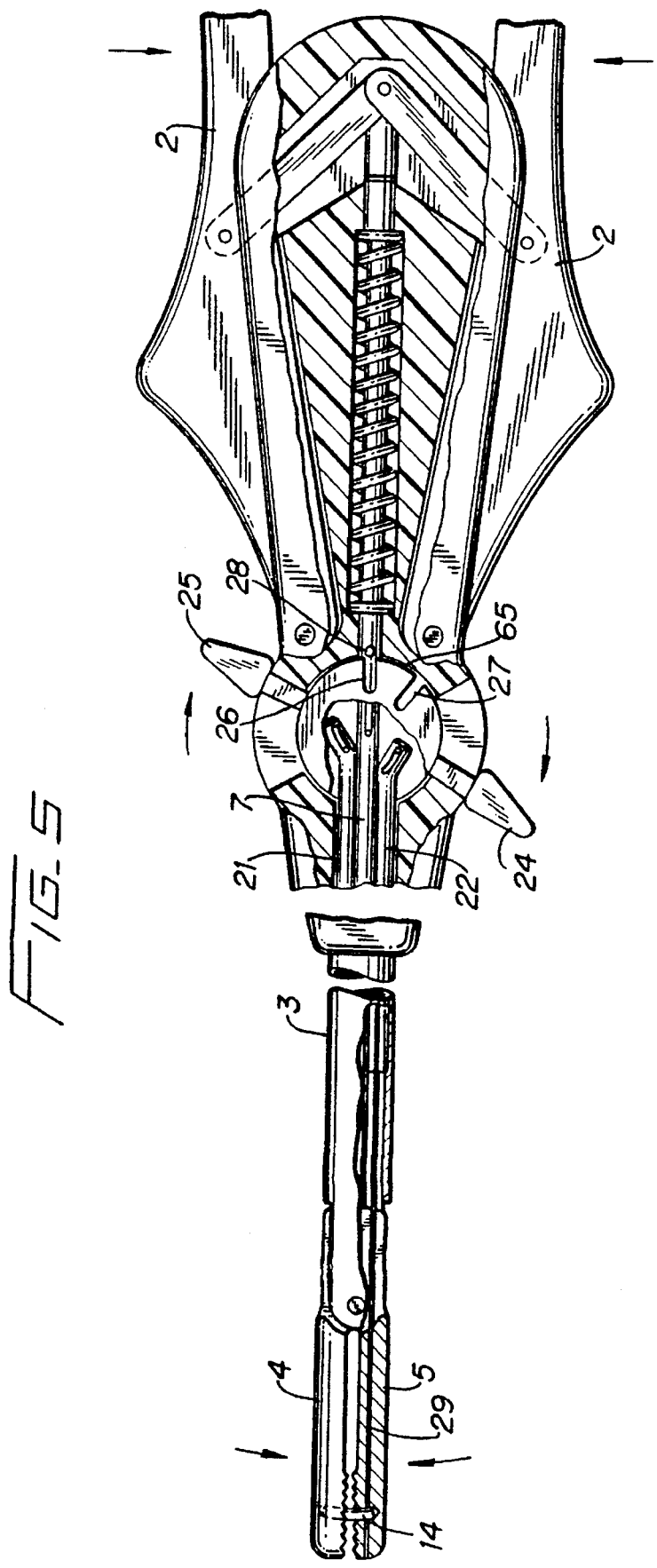

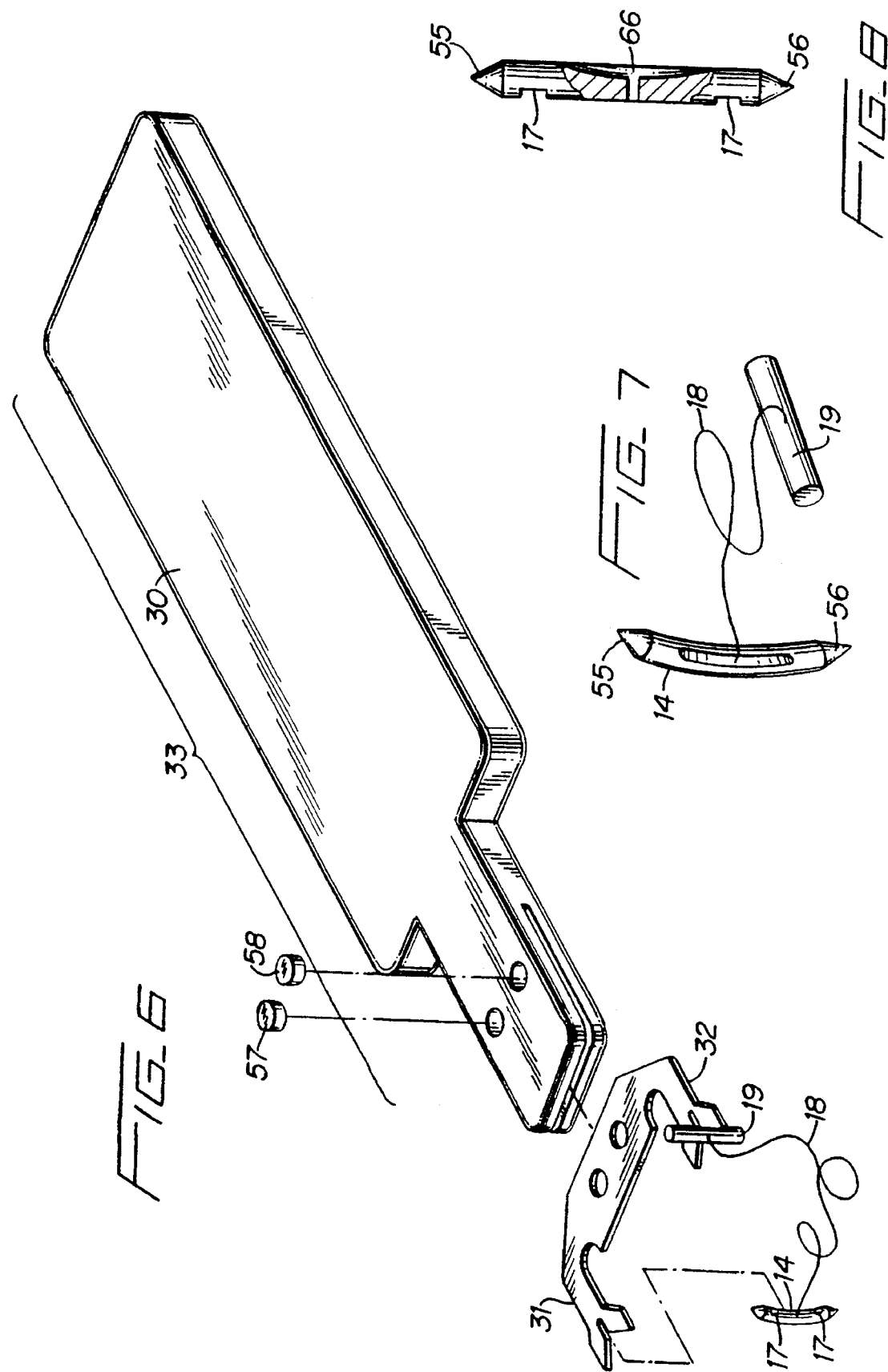

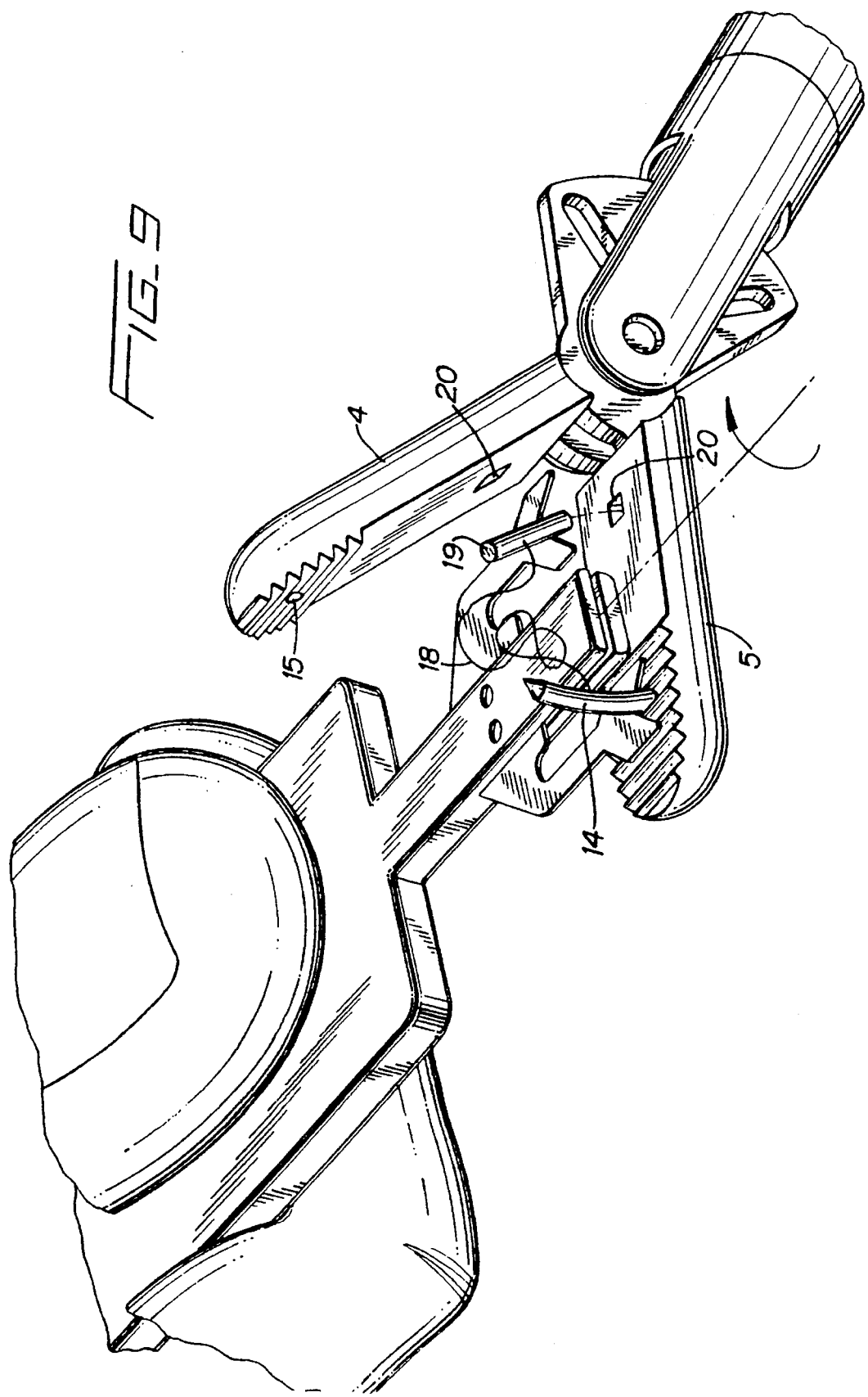

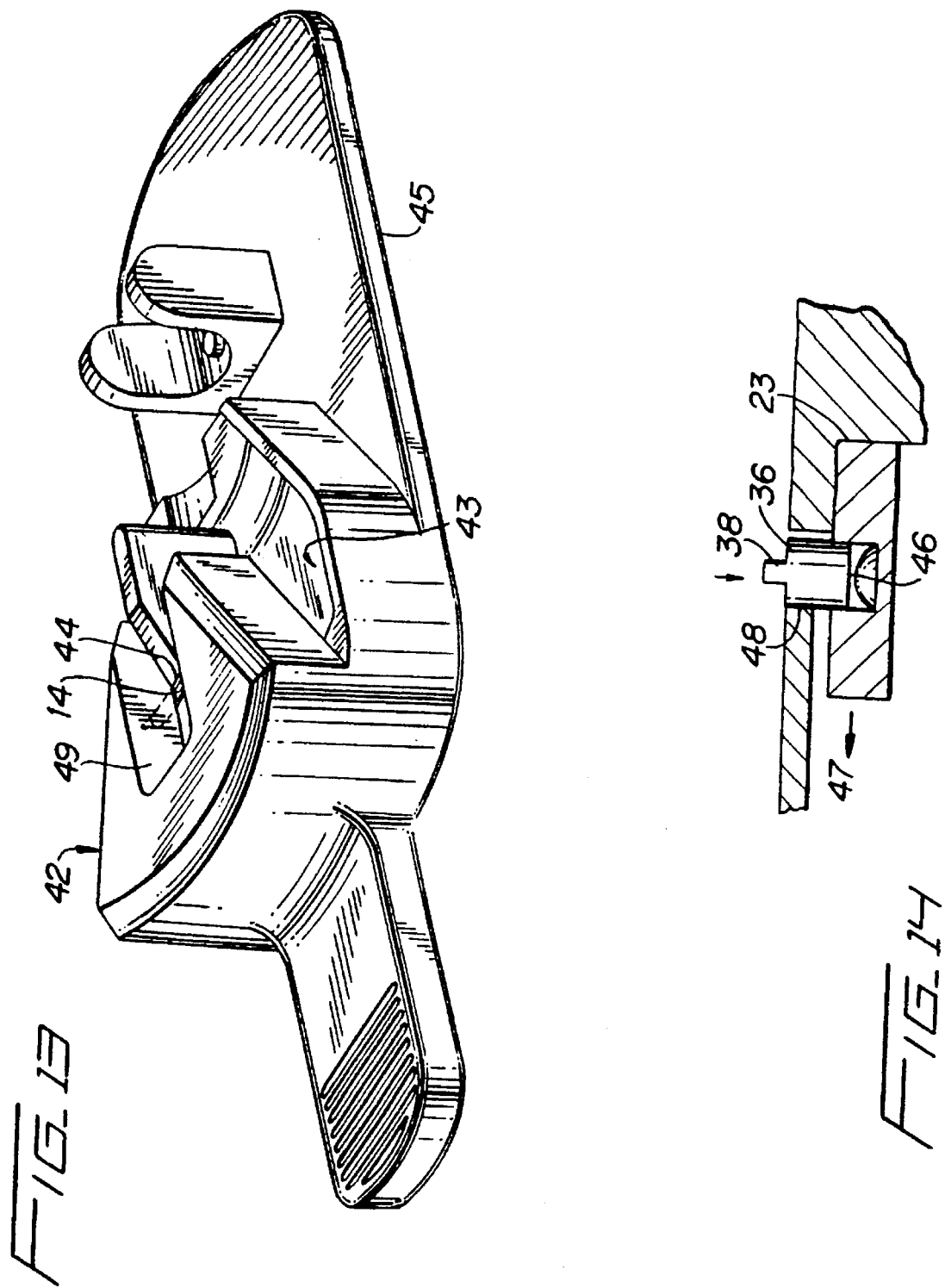

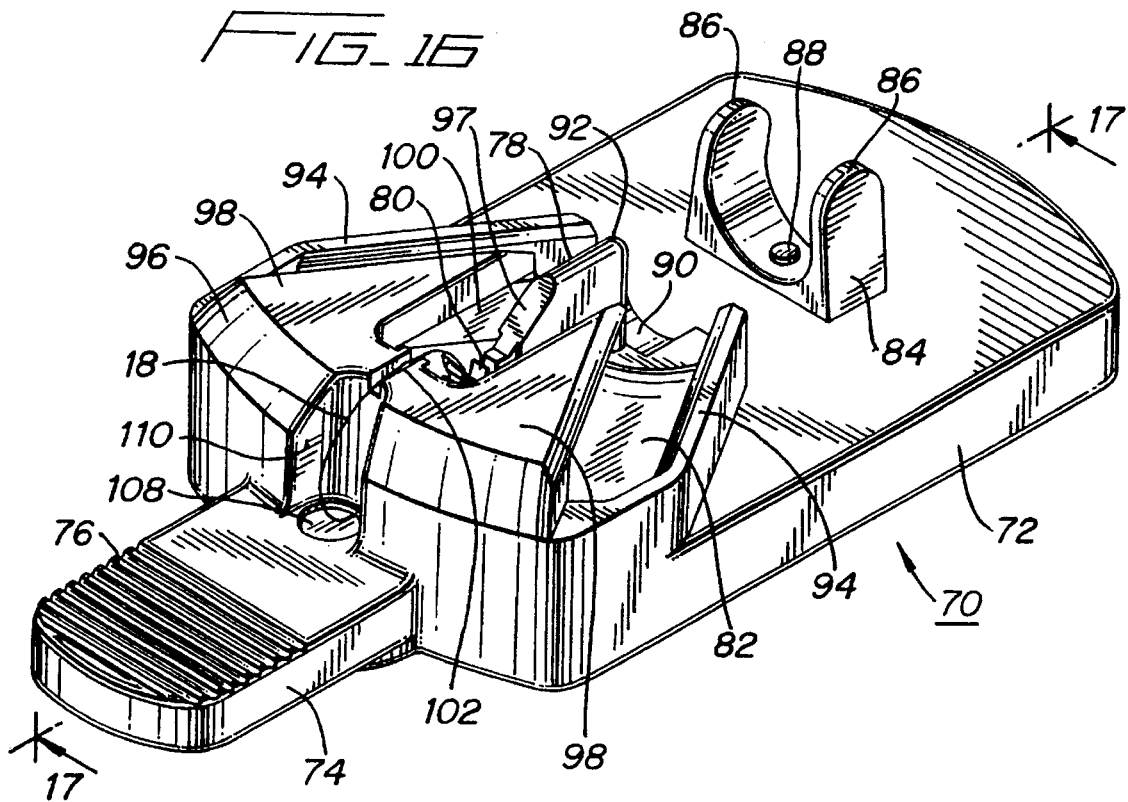
FIG_16
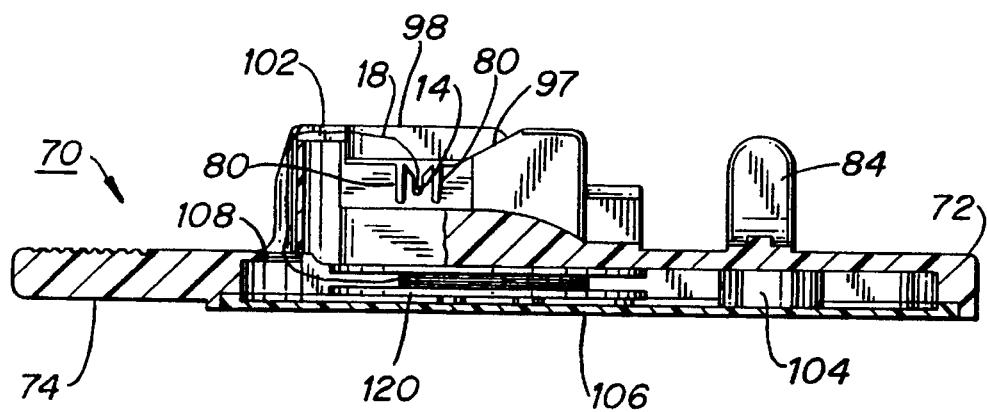
FIG_17

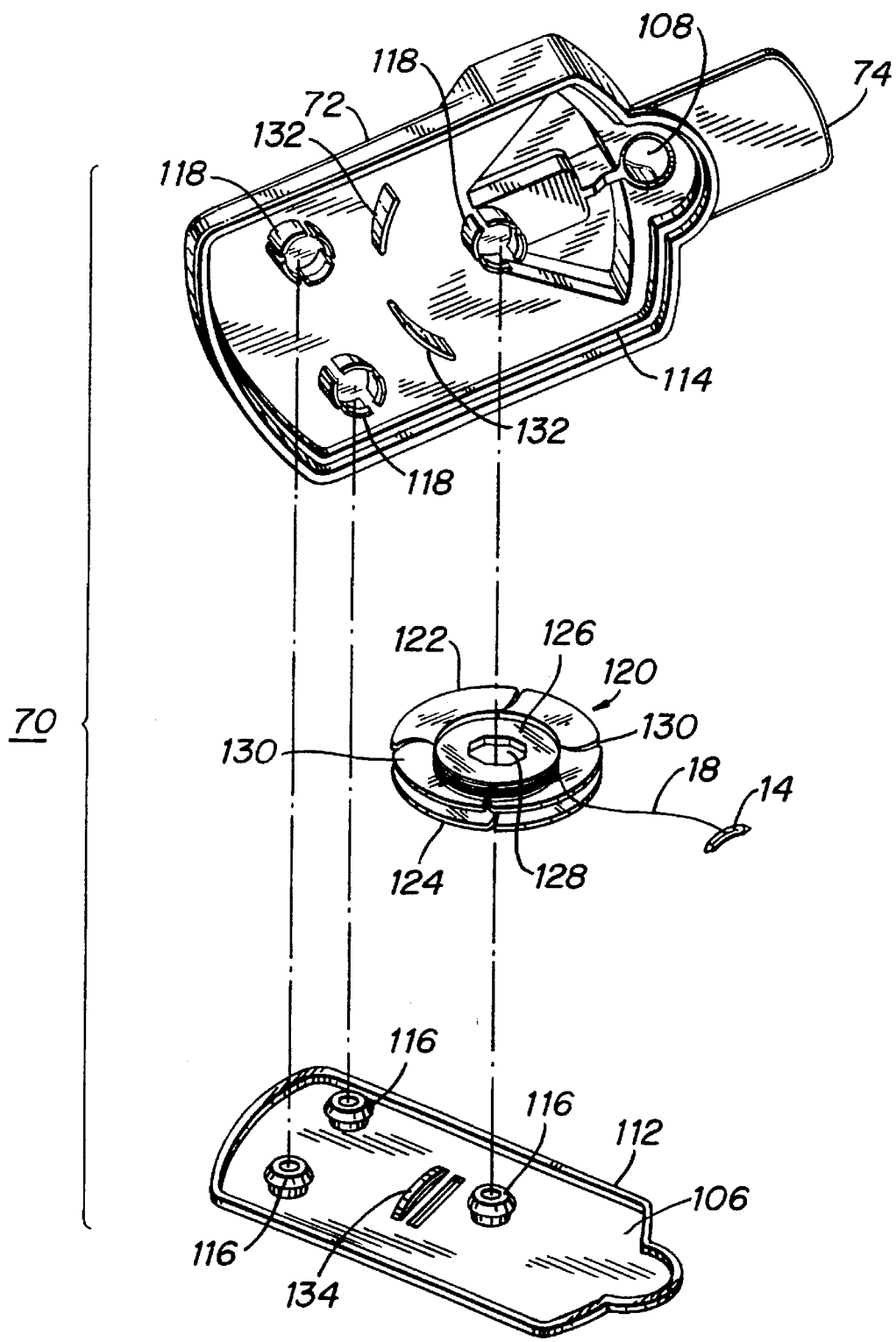

FIG_19
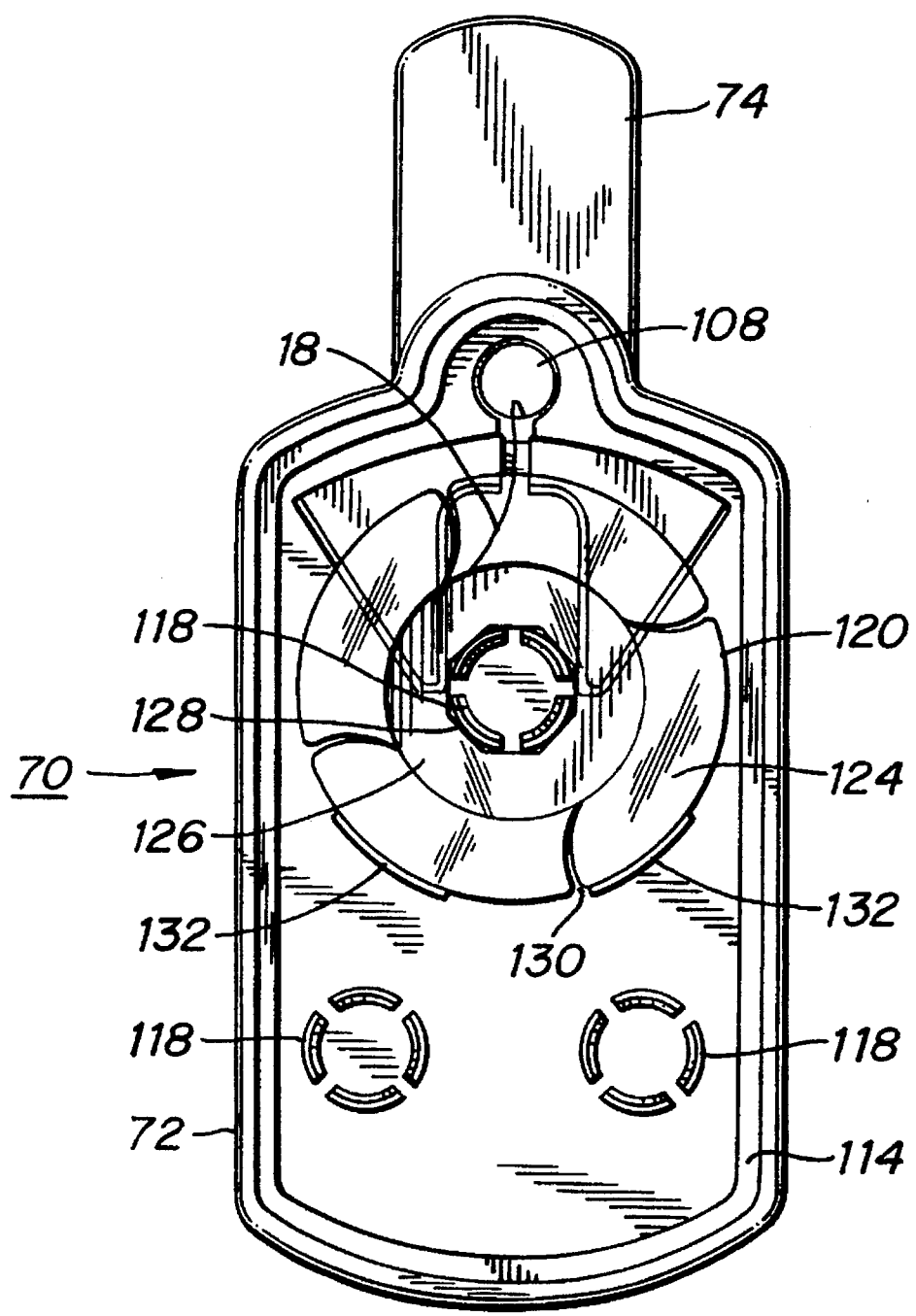

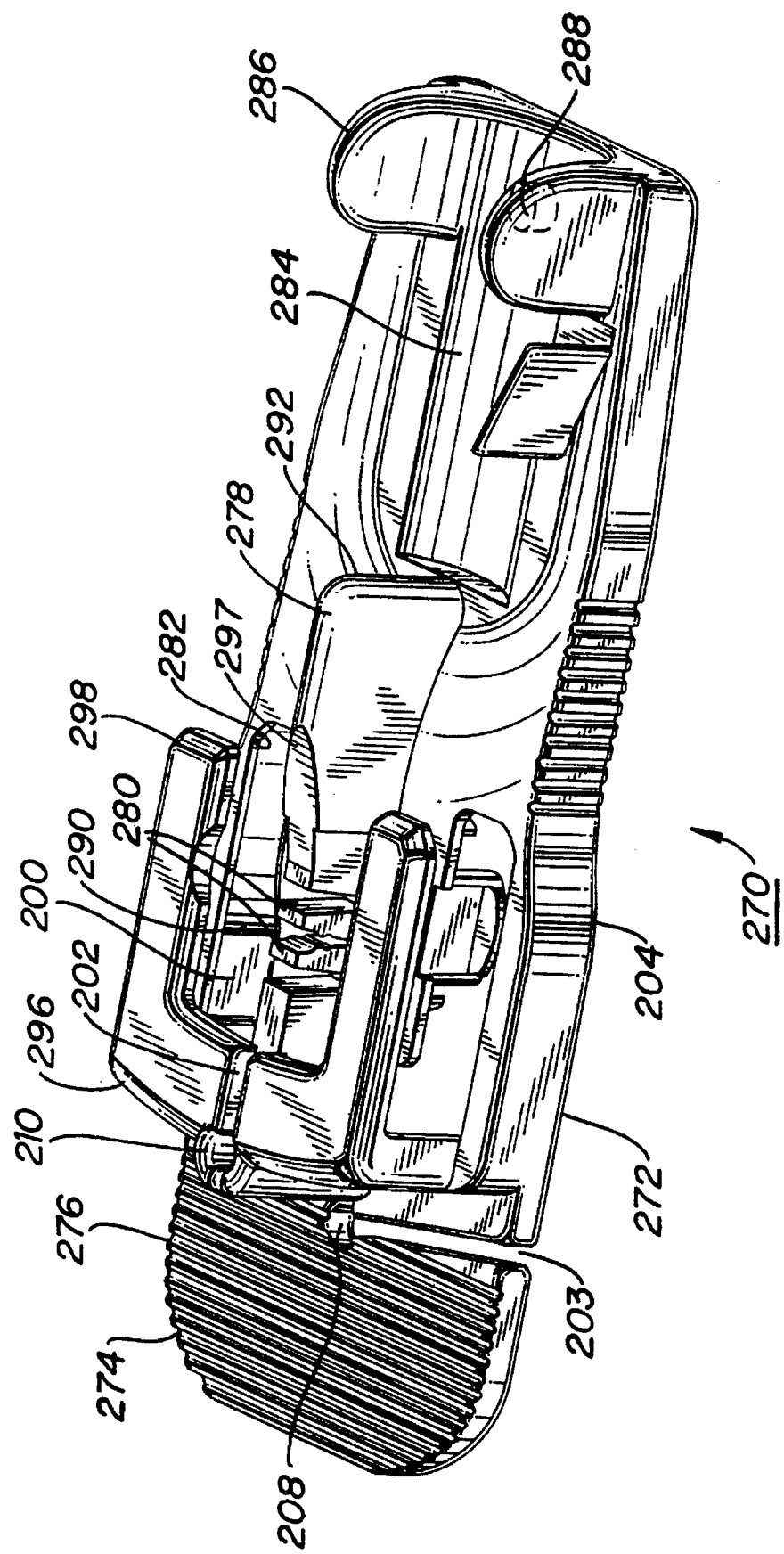

SURGICAL SUTURING APPARATUS WITH LOADING MECHANISM

CROSS REFERENCE TO RELATED APPLICATIONS

This application is a continuation of U.S. patent application Ser. No. 08/293,233 filed Aug. 19, 1994, now U.S. Pat. No. 5,478,344, which is a continuation-in-Part of U.S. patent application Ser. No. 08/134,145, filed Oct. 8, 1993, now abandoned, entitled SURGICAL SUTURING APPARATUS WITH LOADING MECHANISM, the disclosure of which is incorporated by reference herein.

BACKGROUND

1. Technical Field

The device relates generally to surgical instrumentation and, more particularly, to a suturing apparatus and loading unit adapted for use in endoscopic or laparoscopic surgical procedures.

2. Description of Related Art

Endoscopic or laparoscopic procedures are characterized by the use of an elongated cannula structure having a relatively small diameter with a proximal and distal end. The distal end of the cannula is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while the other cannulas may provide conduits for control of specialized surgical instruments designed for performing specific procedural functions.

Many surgical procedures call for placing stitches through tissue, a procedure traditionally accomplished by hand. Laparoscopic suturing presents a particularly challenging task, because it must be accomplished using remote instrumentation through a port that typically averages between five and ten millimeters. One instrument for facilitating laparoscopic suturing is discussed in British Patent Application No. 2260704, published Apr. 28, 1993.

Although the suturing device described in British Patent Application Serial No. 2260704 can be used to place laparoscopic sutures, once the suture is used up, or if a new needle is required, the suturing device must be manually re-loaded, which can be time-consuming. As it is generally considered desirable to place 2 or 3 lines of stitching when performing an anastomosis to provide reinforcement, the laparoscopic suturing device as described in the British Patent Application mentioned above requires manual reloading one or more times. It would be advantageous to provide a laparoscopic suturing instrument to permit quick and efficient reloading of a new needle and suture. A laparoscopic suturing device would also provide an advantage if the jaws could be prevented from moving when the needle is not secured in either jaw, so as to prevent the needle from accidentally dislodging in the body cavity.

SUMMARY

Briefly stated, a surgical apparatus is provided with an elongated body portion, two jaw elements extending from the body portion, securing blades for securing a needle (or similar surgical incision member), the securing blades cooperating with a first recess in each jaw element and a releasing mechanism cooperating with the securing blades for releasing the needle secured by the securing blades. In addition, a locking wheel and pin cooperating with the securing blades prevents the jaw elements from opening unless the needle is secured in at least one jaw, so as to help prevent the needle from accidentally falling from the jaws. The apparatus also has an override mechanism to defeat the locking means, which makes it possible to load a new needle and suture into the device. A loading unit is provided for use with the surgical suturing apparatus to ensure rapid and positive placement of a needle and suture within the jaw elements. The loading unit includes a support member to hold a needle or surgical incision member in a position to be grasped by the jaw elements and a storage member for holding a length of suture attached to the needle. The loading unit may further include structure to align the jaws of the surgical suturing instrument about the needle and a safety mechanism to prevent the removal of the jaws from the loading unit until the needle has been properly grasped by the jaws. As used herein, "needle" or "surgical needle" refers generally to all types of surgical needles, while "surgical incision member" refers more specifically to double pointed needles for use in a surgical suturing apparatus. These together with other advantages will become apparent from the details of construction and operation as more fully hereinafter described and claimed.

BRIEF DESCRIPTION OF THE DRAWINGS

Various embodiments are described herein with reference to the drawings, wherein:

FIG. 1 is a perspective view of one embodiment of a surgical suturing apparatus;

FIG. 2 is an exploded view of the instrument depicted in FIG. 1;

FIG. 3 is an exploded view of the jaw actuating mechanism of the instrument depicted in FIG. 1;

FIG. 4 is a plan view showing the instrument depicted in FIG. 1 with the jaws open and the needle secured in the upper jaw;

FIG. 5 is a plan view showing the instrument depicted in FIG. 1 with the jaws closed;

FIG. 6 is a perspective view of an embodiment of a loading mechanism for a surgical stitching apparatus;

FIG. 7 is a perspective view of the needle, surgical thread and anchor;

FIG. 8 is a plan view of the needle of FIG. 7;

FIG. 9 shows the loading mechanism of FIG. 6 being placed into the jaw of the apparatus;

FIG. 13 is a perspective view of an alternate embodiment of the loading mechanism;

FIG. 14 is a side view of a portion of the mechanism that overrides the lockout mechanism of the instrument depicted in FIG. 1;

FIG. 16 is a perspective view of the loading unit in accordance with the embodiment of FIG. 15 illustrating a length of suture fed from a storage cavity within the loading unit;

FIG. 17 is a side elevational view, partly shown in section, taken along the lines 17—17 of FIG. 16;

FIG. 18 is an exploded perspective view of the loading mechanism of FIG. 15 illustrating a suture reel positioned within the loading unit;

FIG. 19 is a bottom plan view of the loading unit of FIG. 15 with a bottom cover plate removed;

FIG. 23 is a perspective view of an alternate embodiment of a loading mechanism.

DETAILED DESCRIPTION OF PREFERRED EMBODIMENTS

Figure 10:
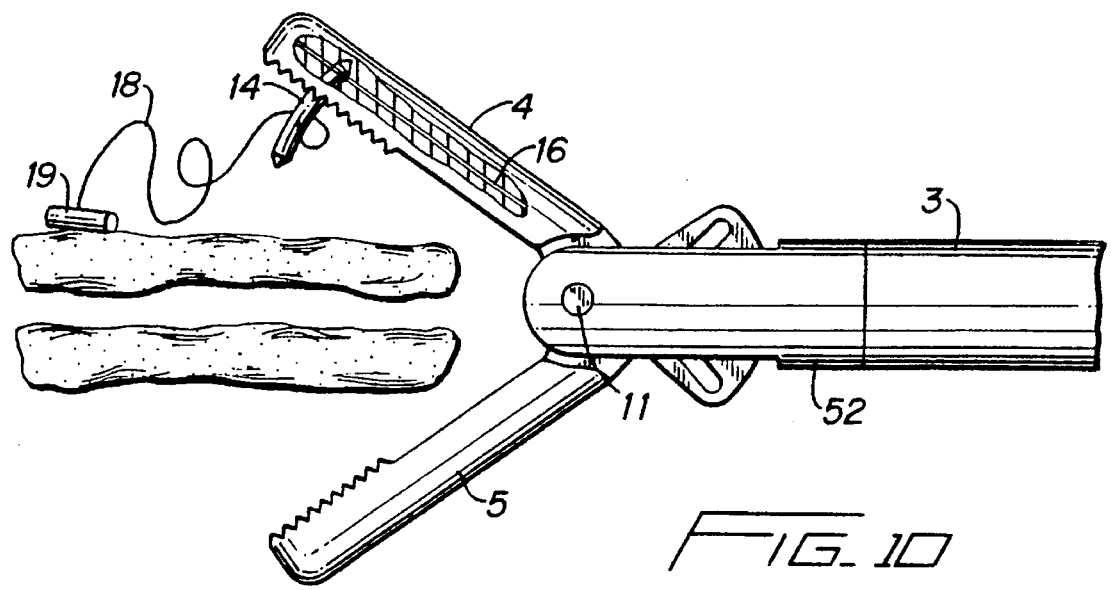
FIGS. 10, 11 and 12 show a plan view of the jaws of the instrument as they draw the needle and connected length of suture through tissue.

Referring now to the drawings and in particular to FIG. 1, there is shown a suturing apparatus generally indicated by reference numeral 1, which has a handle housing 61 with a two-armed handle 2, an elongated tubular housing or body portion 3, and two jaws (or jaw elements) 4 and 5. Handle 2 is used to control the opening and closing of jaws 4 and 5 and may be designed to move in the same plane as jaws 4 and 5 to provide an ergonomic advantage. Handle 2 may also be rotatably connected to body portion 3 to provide further ergonomic advantage. This embodiment is particularly well adapted for use in endoscopic or laparoscopic procedures as the tubular housing 3 is preferably dimensioned to be deployable through a tubular cannula structure, e.g., of 5 mm or 10 mm internal diameter.

Referring to FIG. 2, handles 2 are connected to rod 7 by a pair of links 33 and 34 and pins 49, 50 and 51. Center rod 7 is spring biased distally by spring 6. Spring 6 fits around center rod 7 and rests in channel 63 of housing 61. When the handles 2 are squeezed, center rod 7 moves backward (proximally), causing spring 6 to be compressed. Referring to FIG. 3, the distal end of center rod 7 has a pin 8 which rides in a cam slot 9 and 10 in each of the jaws 4 and 5. Jaws 4 and 5 are pivotally connected to each other by pin 11 extending through holes 12 and 13 and through holes 53 and 54 of support 52. When center rod 7 is pulled back, pin 8 is also pulled back in cam slots 9 and 10, camming jaws 4 and 5 closed.

Referring to FIG. 3, each jaw is adapted to receive needle 14 (FIG. 7) in recess 15. Needle 14 is depicted throughout the figures as a surgical incision member (as defined above), however, the use of other varieties of surgical needles is also contemplated. When jaws 4 and 5 are closed as shown in FIG. 5, the needle 14 sits in the recess 15 in both jaws. When the jaws are opened, the needle 14 is retained in one or the other recess 15 depending on which blade 16 or 29 intersects the needle 14 through recess 17 (see FIG. 8). As shown in FIG. 4, blade 16, for example, cooperating with upper jaw element 4 has been extended into recess 17 to secure needle 14. Alternatively, blade 29 may intersect needle 14 through recess 17, securing needle 14 in jaw 5. The movement of blades 16 and 29 to engage needle 14 will be described in more detail below.

On either side of the center rod 7, side rods 21 and 22 sit inside tubular housing 3 and are connected at their proximal ends to a wheel 23 movably housed inside handle housing 61. The two halves of housing 61 are secured by pins 30. Wheel 23 has two arms 24 and 25 projecting from either side that allow the operator of the apparatus to turn wheel 23. To transfer needle 14 from jaw 4 to jaw 5, the jaws are closed and wheel 23 is rotated by turning side and 25 clockwise so that side rod 21 is pulled back and side rod 22 is pushed forward. The side rods 21 and 22 are connected to blades 16 and 29, respectively. Therefore, when side rod 22 is pushed forward, blade 29 is pushed forward and engages needle 14 by extending into recess 17 to secure needle 14 in jaw 5. While blade 29 is in a forward position, blade 16 is in a retracted position, thus blade 16 does not contact needle 14, thereby allowing release of the needle from jaw 4. Similarly, side arm 24 may be turned counterclockwise, sliding side rod 21 and blade 16 forward and side arm 22 and blade 29 backward, thereby securing needle 14 in jaw 4 and allowing release from jaw 5. Blades 16 and 29 have notches 40 and 41, respectively, in their distal ends. These notches remain behind (proximal to) recesses 15 in jaws 4 and 5 unless the override mechanism, discussed below, is activated. When the override mechanism is activated, notches 40 and 41 align with recesses 15.

Turning now to the lockout mechanism which prevents jaws 4 and 5 from opening unless blade 16 or 29 has moved into position to secure needle 14, as shown in FIG. 2, a pin 28 extends through rod 7 which is housed proximally in wheel 23. Wheel 23 has notches 26 and 27 and abutment surface 65 therebetween. When wheel 23 is positioned so that pin 28 is aligned with the mouth of one of the notches 26, 27, the jaws 4, 5 can be opened because pin 28 has room to move forward into that notch; when wheel 23 is positioned so that pin 28 rests against abutment surface 65, jaws 4 and 5 cannot be opened because pin 28 is stopped by abutment surface 65, i.e., it does not have room to move forward.

In the initial position shown in FIG. 4, the handles 2 are open, as are jaws 4 and 5. Needle 14 is retained in jaw 4 by blade 16. In this position, pin 28 is forward in notch 27. To close jaws 4, 5 and suture body tissue, handles 2 are squeezed together, causing rod 7 and associated pin 28 to move rearwardly so that pin 28 is at the mouth of notch 27. Wheel 23 is then rotated using arms 24 or 25 to pass the needle 14 from jaw 4 to jaw 5 as described above. The rotation of wheel 23 slides pin 28 along abutment surface 65 to the mouth of notch 26. The handles can then be released, causing pin 28 to move forward into notch 26 under the force of spring 6 (discussed above), consequently moving rod 7 forward to open the jaws.

Therefore, when wheel 23 is positioned so that pin 28 is aligned with notch 26, it causes side rod 22 to be pushed into a forward position, placing blade 29 in a forward position so as to intersect needle 14 through recess 17, thereby securing needle 14 in jaw 5. When wheel 23 is positioned so that pin 28 is aligned with notch 27, it causes side arm 21 to be pushed into a forward position, placing blade 16 in a forward position so that it intersects needle 14 though recess 17, thereby securing needle 14 in jaw 4.

If the user attempts to release the handles 2 when the pin 28 is not aligned with the mouth of either notch, i.e., when wheel 23 is in position so that pin 28 is resting against (aligned with) abutment surface 65, pin 28 cannot slide forward and consequently rod 7 cannot slide forward to open the jaws 4 and 5. Thus, the locking mechanism of this apparatus prevents jaws 4 and 5 from opening if needle 14 is not secured in one of the jaws by the respective blade.

Needle 14 as shown in FIG. 7 is curved, has two pointed ends 55 and 56 and is connected to a portion of surgical suture 18 in the center of needle 14. Channel 66 holds an end of the suture. To retain the suture in the needle, the suture may either be glued into channel 66 or the needle itself may be crimped. A straight needle as shown in FIG. 8 may also be utilized, and the suture can be connected adjacent one of the ends (not shown). A single-pointed needle could also be alternatively provided (not shown). The opposite end of suture 18 may also have an anchor 19 affixed thereto for securing the suture in tissue.

Figure 11:
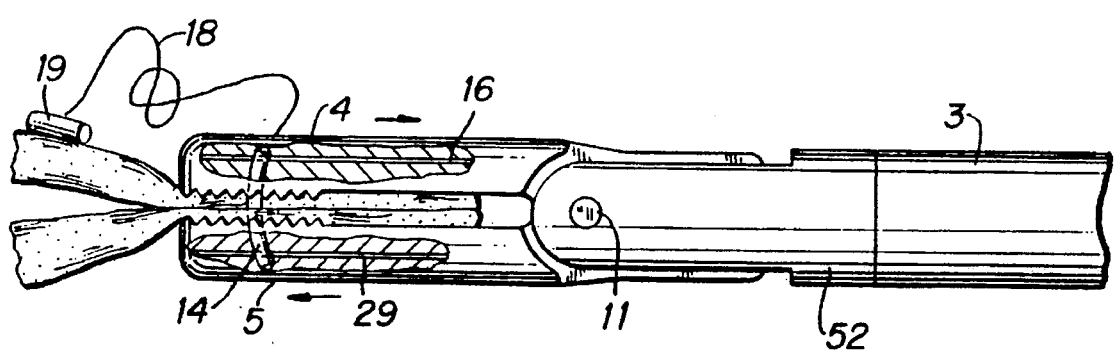
Figure 12:
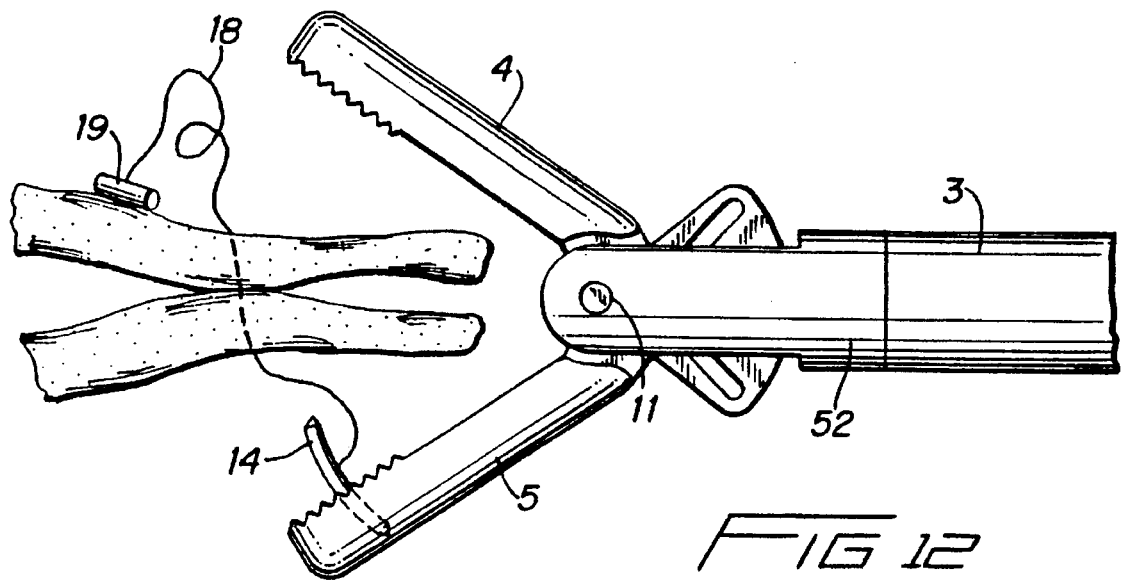

Referring to FIGS. 10, 11 and 12, to operate the suturing apparatus, the open jaws 4, 5 are positioned around the tissue to be sutured. Note that needle 14 is shown held securely in jaw 4 by blade 16. Handles 2 are squeezed, closing the jaws 4, 5 around the tissue and piercing it with needle 14, which is held securely in jaw 4 by blade 16. As needle 14 pierces the tissue, it is guided into a recess 15 in the opposite jaw 5. If the jaws are open, pin 28 is positioned forward in notch 26 or 27 as described above, and consequently wheel 23 cannot move until the jaws are closed and pin 28 can then travel along abutment surface 65. With the jaws closed, wheel 23 may be moved by turning side arm 25 clockwise, thereby sliding blade 16 out of one end of the needle 14 and simultaneously sliding blade 29 into the other end of the needle. This clockwise movement slides pin 28 from the mouth of notch 27 to the mouth of notch 26 as described above. Thus, by turning side arm 25 (and wheel 23), needle 14 is released from jaw 4 and engaged in jaw 5. The needle 14 will then be positioned in the jaw 5, drawing suture 18 through the tissue. Anchor 19 will rest on the tissue, thereby securing suture 18 in the tissue. The jaws 4 and 5 are then opened by releasing the handles. If the needle 14 is double-pointed, the instrument is ready to make another stitch. To do so, the handles 2 are squeezed and the jaws are again closed. After closing the jaws to make the second stitch, the needle 14 can be passed back to jaw 4 by rotating side arm 24 of wheel 23 to slide blade 16 distally and blade 29 proximally. If the needle has only one point, the needle must be transferred back to the opposite jaw (by closing the jaws and rotating wheel 23) before the instrument is ready to make another stitch.

In order to load the suturing apparatus, jaws 4 and 5 must be opened and still allow needle 14 to be removed and a replacement needle to be loaded into slot 15. This cannot be accomplished if either blade 16 or 29 is intersecting slot 15 in accordance with the securing mechanism described above. Therefore, a mechanism to override the lockout mechanism described above is provided, as shown in FIGS. 2 and 14. U-channel 35 swaddles wheel 23. Spring 34 is seated within channel 64 of housing 61 and is proximal to U-channel 35 and wheel 23. Rod 7 extends through spring 34, hole 59 in U-channel 35 and wheel 23. Plungers 36 and 37 each rest in hole 60 on either side of wheel 23 and each plunger extends through U-channel 35. Each plunger 36, 37, rests upon a spring washer 46, which also rests in hole 60 in wheel 23. Plungers 36 and 37 have a smaller-diameter knobs 38 and 39, respectively, extending therefrom and through housing 61.

As shown in FIGS. 2 and 14, housings 61 have channels 62 in which knobs 38 and 39, respectively, may move back and forth freely. Plungers 36 and 37, however, rest against surface 48 in housing 61. When knobs 38 and 39 are pushed down, spring washers 46 compress, plungers 36 and 37 clear surfaces 48 and ride forward (distally) into recesses 47, propelled by the energy of compressed spring 34.

Therefore, to operate this override mechanism, side arms 24 and 25 are positioned so that pin 28 is abutting abutment surface 65 and cannot ride forward into notches 26 or 27. Knobs 38 and 39 are pushed down, thereby causing wheel 23 to ride forward into recesses 47 of housing 61. As wheel 23 rides forward, so do pin 28 and rod 7, thereby allowing jaws 4 and 5 to open.

When wheel 23 is propelled forward as described above, side rods 21 and 22 and blades 16 and 29 are driven forward sufficiently so that notches 40 and 41 align with recess 15 in each jaw. When notches 40 and 41 align with recess 15, blades 16 and 29 are technically in a forward position (which allows the jaws to be opened because the lockout mechanism described above is only actuated if neither blade is in a forward position). In this position, however, recesses 15, instead of being intersected by blades 16 and 29, are aligned with notches 40 and 41 so that recesses 15 are clear all the way through in each jaw, thereby allowing the old needle 14 to be removed from the instrument and a new needle 14 to be replaced. Thus, the lockout mechanism discussed above has been defeated by the override mechanism, because the jaws 4, 5 are open, and yet the needle 14 is not secured. After the new needle has been inserted, side arms 24 and 25 can be pulled proximally, compressing spring 34 and re-engaging lower knobs 36 and 37 with surface 48, thereby rearming the lockout mechanism of this instrument.

Referring to the loading mechanism for replacing the needle, suture and anchor of the present stitching apparatus shown in FIG. 13, needle 14 is positioned in notch 44 and recesses 42 and 43 of the loading mechanism are configured to receive jaws 4 and 5. When jaws 4 and 5 are closed, the needle 14 becomes engaged in jaw 4 and the closed jaws are removed from the loading mechanism by lifting them through recess 49. The body portion of this loading mechanism 45 may be hollow, thereby holding a package containing suture and anchor inside it.

FIG. 6 shows another embodiment of a loading mechanism 33 for replacing the needle, suture and anchor of the present stitching apparatus. The loading mechanism consists of handle 30 and arms 31 and 32 attached thereto via fasteners 57 and 58. Each arm is adapted to hold either an anchor/positioning element 19 or a needle 14. The anchor/positioning element 19 and the needle 14 are preferably approximately the same diameter so that both arms 31 and 32 may be of similar dimension.

Referring to FIG. 9, each jaw may be adapted to hold anchor 19 shown in FIG. 6. Recess 20 is one adaptation suitable to hold the suture anchor. The distance between the needle's recess 15 and the anchor's recess 20 approximately equals the distance between the needle 14 and anchor 19 in the loading mechanism to facilitate proper loading. Suture anchor 19 can be fixedly attached to needle 14 by suture 18. Suture anchor 19 may also help guide and position needle 14 into recess 15. If anchor 19 is not properly placed in recess 20, jaws 4 and 5 cannot close. If anchor 19 is properly placed, however, this placement helps guide the position of needle 14 into recess 15. Alternatively, a separate positioning element may be provided. In yet another embodiment, positioning element 19 is fixedly attached to loading mechanism 33 and is placed into recess 20 for positioning purposes, but is drawn away when the loading mechanism 33 is removed from the suturing apparatus.

To reload a needle, anchor and suture into the apparatus, the override mechanism described above would be activated and the old needle removed. As shown in FIG. 9, to reload the apparatus utilizing loading mechanism 33, mechanism 33 is held perpendicular to the bottom open jaw 5 and the needle 14 and the anchor/positioning element 19 are placed into their respective recesses (15 and 20) one at a time. After the needle 14 and anchor/positioning element 19 are placed in their respective recesses, the jaws 4, 5 are closed, and the loading mechanism 33 is pulled away, leaving the needle 14 and anchor 19 in place.

Referring now to FIGS. 15 to 22, there is disclosed an alternate embodiment of a loading unit suitable for use with a surgical suturing apparatus. Loading unit 70 is provided to rapidly and positively seat a needle or surgical incision member and suture such as, for example needle 14 and suture 18, within the jaws of the surgical suturing apparatus. The needle in these figures is depicted as a surgical incision member, although the use of other varieties of surgical needles is also contemplated.

Figure 15:
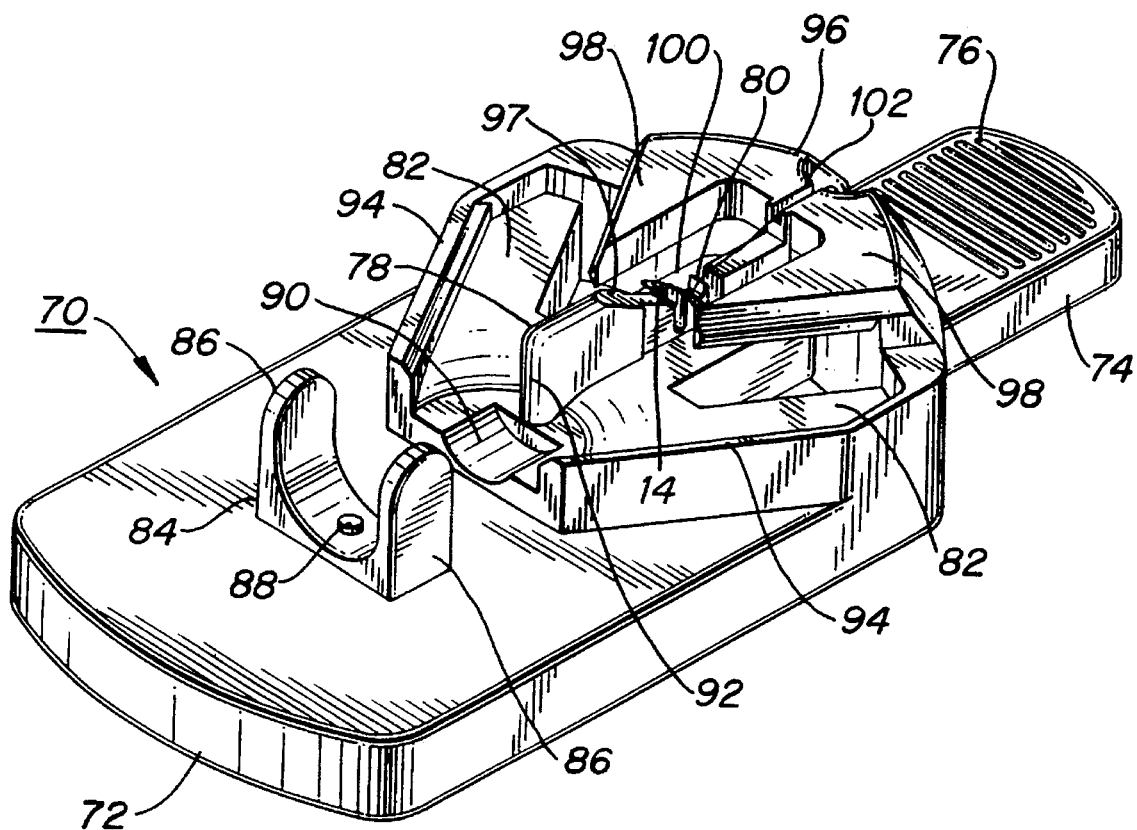
FIG. 15 is a perspective view of an alternate embodiment of a loading mechanism illustrating a surgical incision member being supported within the loading unit and alignment structure for guiding a surgical suturing apparatus into position on the loading unit.

Referring now to FIGS. 15 and 16, loading unit 70 generally includes a body portion 72 having a handle or finger tab 74 extending proximally therefrom. As used herein with reference to loading unit 70, the term "proximally" refers generally in the direction toward the holding hand of the user. Preferably finger tab 74 may include a plurality of ridges 76, or be otherwise textured, to enhance the gripping ability of the user.

Loading unit 70 is provided to support needle 14 in a manner to facilitate gripping or loading needle 14 into a surgical suturing instrument. Thus, loading unit 70 includes a needle support member 78 formed on body portion 72 to support or suspend needle 14 by a central portion thereof. Preferably support member 78 includes a pair of flexible fingers 80 which hold a central portion of needle 14. Apparatus receiving structure may be provided to guide jaws 4 and 5 adjacent support member 78. The apparatus receiving structure may include a pair of jaw support shelves 82 which are provided adjacent and below either the side of support member 78 to define a pair of recesses adjacent thereto. Shelves 82 further serve to align a pair of jaw members positioned thereon in a manner to grasp needle 14.

Additionally, the apparatus receiving structure may include various other alignment structure to guide or orient the jaws of a surgical suturing apparatus into position on loading unit 70 in order to grasp and remove needle 14. For example, an elongate member alignment structure 84 may be provided to guide a barrel housing or elongate portion of a suturing instrument into position on loading unit 70. Alignment structure 84 generally includes a pair of side tabs 86 which surround the suture apparatus elongate portion. Additionally, a support stud 88 may be provided on a bottom edge of alignment structure 84 to maintain the elongate portion in proper vertical alignment with a corresponding recess in the suture apparatus elongate portion. Further, a recess such as for example, recess or cup 90, may be provided between a distal end of jaw support shelves 82 to support the distal end of the elongate portion. When inserted in alignment structure 84, the distal end of the surgical summing apparatus elongate portion will abut a distal end 92 of needle support member 78 to limit advancement of the jaws within the loading unit.

Various structure or safety features may be provided to ensure that needle 14 may not be removed from loading unit 70 until needle 14 has been firmly grasped by completely closing the surgical instrument suturing jaws. A pair of sidewalls 94 are provided on jaw support shelves 82 and generally taper towards cup 90. Sidewalls 94 aid in ensuring consistent horizontal alignment of the jaws on support shelves 82 and additionally aid in preventing premature longitudinal withdrawal of the suture apparatus out from the loading unit.

The safety mechanism 96 is provided to prevent lifting of the jaws, and thus lifting of needle 14 out of loading unit 70 before needle 14 has been firmly grasped by the jaws. Safety mechanism 96 generally includes a pair of triangular blocking members 98 which are suspended above and adjacent either side of needle support member 78. Blocking members 98 prevent vertical movement of the jaws out of loading unit 72 until the jaws are closed, thereby firmly grasping needle 14. Additionally a ramped face 97 on support member 78 in cooperation with side walls 94 prevent longitudinal withdrawal of the jaws from loading unit 70. Once the jaws of a surgical suturing apparatus have been firmly and positively closed about needle 14, jaws may be lifted vertically through a gap 100 formed between members 98 in order to remove needle 14 from loading unit 70. Thus, members 98 in conjunction with ramped face 97 and side walls 94 aid in ensuring that a needle 14 is not removed from the loading unit 70 until jaws have been fully closed and firmly grasp needle 14.

As noted hereinabove, needle 14 is preferably provided with a length of suture material 18. It is desirable to maintain the length of suture material 18 in a orderly and secure fashion until such time as needle 14 is removed from loading unit 70. Loading unit 70 includes a guide notch 102 which guides a length of suture into a hollow body cavity 104 of loading unit 70 (FIG. 17). Still referring to FIGS. 16 and 17, hollow body cavity 104 is formed between body portion 72 and a body portion bottom plate 106. Suture 18 extends through an aperture 108 formed in a distal portion of finger tab 74 and extends into hollow body cavity 104. Additionally, a channel 110 may be provided in body portion 72 to guide the length of suture between notch 102 and hollow body cavity 104. Thus, the length of suture 18 is nearly and securely stored within loading unit 70 prior to removal of needle 14.

Referring now to FIGS. 17 and 18, bottom plate 106 is affixed to body portion 72 in friction fit fashion by way of a lip i 12 on body portion 106 which engages a recessed edge 114 of body portion 72. Additionally, a plurality of male members 116 formed in bottom plate 106 may engage corresponding female members 118 in body portion 72 to securely fasten bottom plate 106 to body portion 72. It will be noted that various other ways of removably yet firmly securing bottom plate 106 to body portion 72 may be provided.

As noted hereinabove, loading unit 70 provides structure for neatly and securely maintaining at least a portion of a length of suture material within loading unit 70. Preferably a storage member, such as, for example, suture reel 120, is movably disposed between bottom plate 106 and body portion 72. Suture reel 120 generally includes a top portion 122 and a bottom portion 124 held in spaced apart relation by a central portion 126. As shown in FIGS. 17–19, at least a portion of a length of suture material is disposed between top portion 122 and bottom portion 124 and preferably wrapped around central portion 126. As shown, central portion 126 of suture reel 120 preferably includes a bore 128 which surrounds male member 116 and female member 118 to allow suture reel 120 to rotate as suture 18 is withdrawn. Slits 130 may be provided on top and bottom portions 122 and 124, respectively, to temporarily secure a section of suture material on suture reel 120. Additionally, a pair of reel guides 132 may be formed on a bottom surface of body portion 72 to guide suture reel 120 in rotation and to prevent excess unravelling of suture material. As best shown in FIG. 18, a flexible tensioning member 134 may be formed in bottom plate 106 to provide fictional engagement with suture reel 120 in order to prevent inadvertent unraveling of suture material 18.

As discussed hereinabove, loading unit 70 is provided to rapidly and positively load needle 14 and length of suture 18 into the jaws of a surgical suturing apparatus, such as, for example, jaws 4 and 5 of suturing apparatus 1, described hereinabove. Loading unit 70 is particularly suited to ensure that needle 14 is not removed from loading unit 70 until such time as needle 14 is firmly and completely seated within recesses 15 of jaws 4 and 5.

Figure 20:
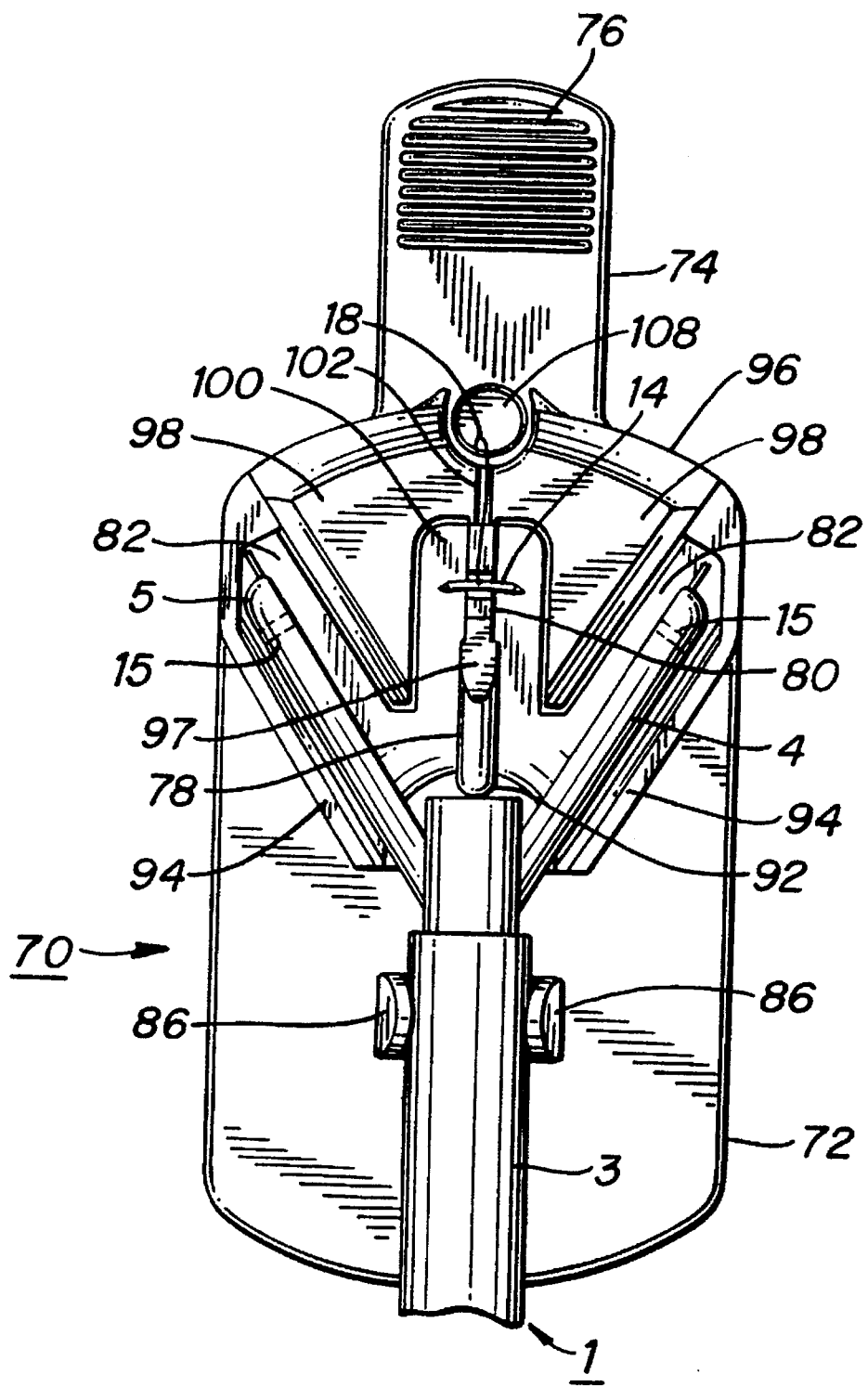
FIG. 20 is a top plan view of the loading unit of FIG. 14 illustrating a portion of a surgical suturing apparatus positioned in the loading unit.
Figure 21:
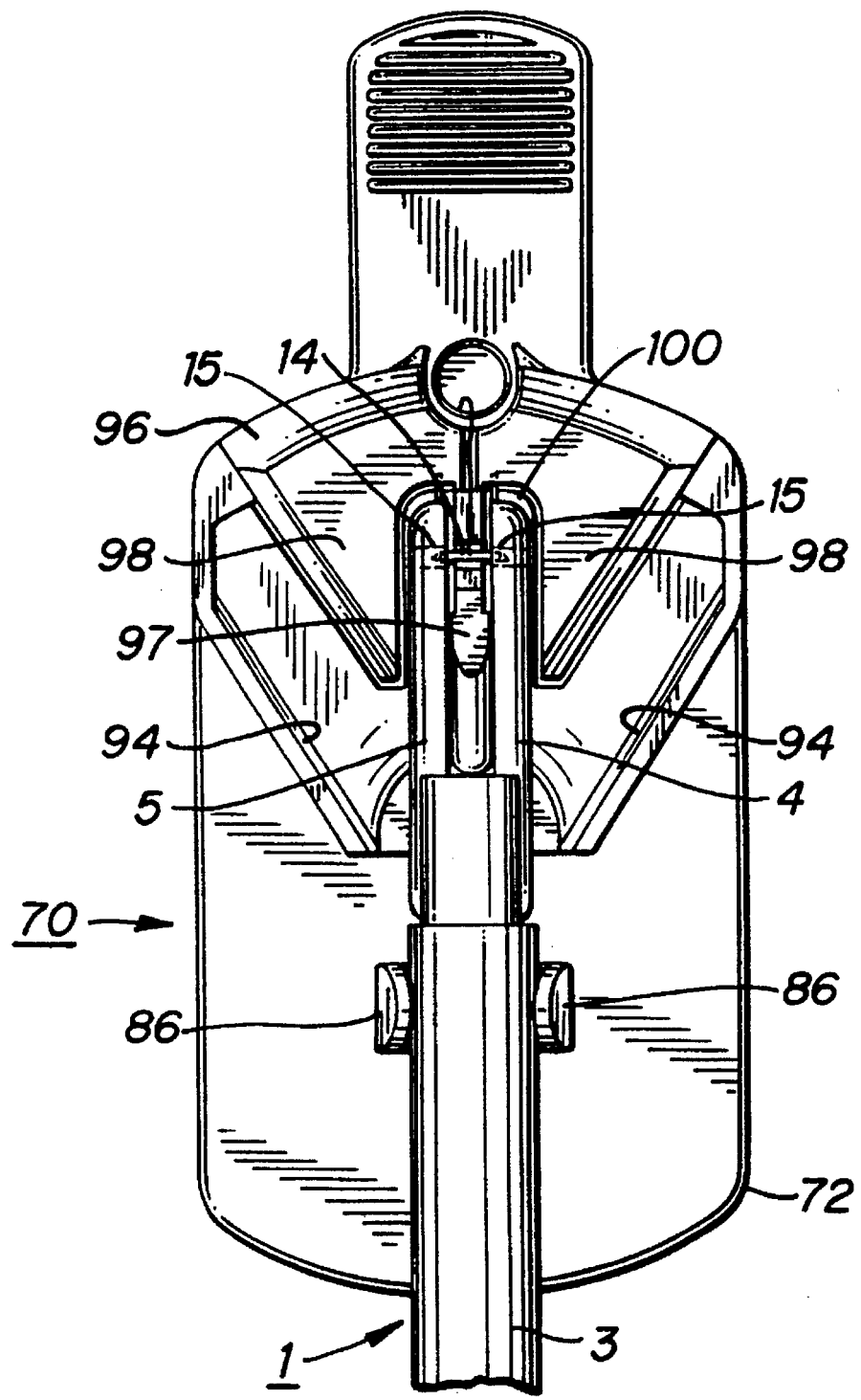
FIG. 21 is a view similar to FIG. 20 illustrating the jaws of a surgical suturing apparatus grasping a surgical incision member.
Figure 22:
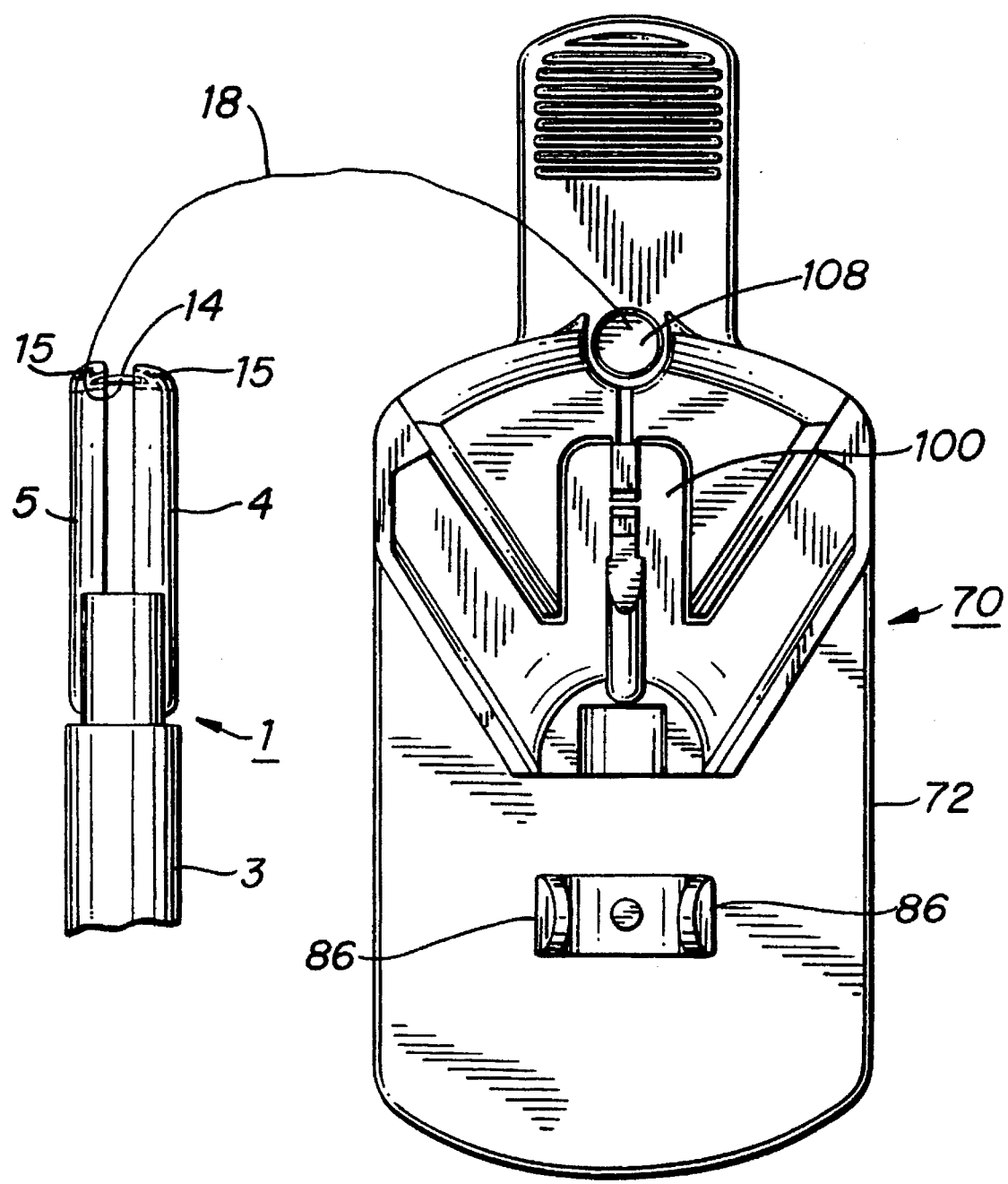
FIG. 22 is a view similar to FIGS. 20 and 21 illustrating the surgical incision member removed from the loading unit by the jaws and the length of suture being drawn out of the storage member.

Referring now to FIGS. 20–22, and initially to FIG. 20, needle 14 is initially positioned on support member 78 and grasped by fingers 80. Suture 18 extends from a central portion of needle 14 through notch 102 and aperture 108 into the hollow body cavity 104 of loading unit 70. In use, the user firmly grasps loading unit 70 by handle 74. As noted above, ridged surfaces 76 ensure a consistent and firm grip on loading unit 70. A surgical suturing apparatus 1 is inserted into loading unit 70 by positioning elongate member 3 between side tabs 86. A distal end of elongate member 3 abuts end 92 of support member 78 to limit the degree to which suturing apparatus 1 is inserted into loading unit 70. When positioned in loading unit 70, jaws 4 and 5 are initially placed in an open condition on jaw support shelves 82.

Referring now to FIGS. 20 and 21, once suturing apparatus 1 has been positioned on loading unit 70, arms 4 and 5 are pivoted to a closed position, in a manner more fully described hereinabove, such that recesses 15 in jaws 4 and 5 surround the suspended ends of needle 14. As further noted hereinabove, blade 16 or 29 (not shown) is moved into position to firmly grasp needle 14. As most clearly shown in FIG. 21, suturing apparatus 1 may now be lifted vertically through gap 100 between arms 98 and to remove elongate portion 3 is pulled free of its friction fit contact with side tabs 86 the now "loaded" suturing apparatus 1 from loading unit 70.

As discussed hereinabove, safety mechanism 96 ensures that suturing apparatus 1 cannot be removed from loading unit 70 until the jaws 4 and 5 have been fully closed about needle 14. For example, should jaws 4 and 5 only be partially closed towards needle 14, jaws 4 and 5 will be unable to pass through gap 100 and thus will not be able to pass between members 98. Thus, suturing apparatus 1 cannot be removed from loading unit 70 in a vertical direction. Further, referring to FIGS. 20 and 21 in conjunction with FIG. 17, should the user attempt to draw summing apparatus 1 out of loading unit 70 in a longitudinal direction, partially open jaws 4 and 5 will cam against side walls 94 preventing further longitudinal withdrawal of suturing apparatus 1. Additionally, and as most clearly seen in FIG. 17, should jaws 4 and 5 be partially closed and beneath members 98, ramped surface 97 of support member 78 will prevent the needle from being removed from fingers 80 and thus prevent suturing apparatus 1 from being withdrawn from the loading unit 70 in a horizontal direction. Thus, in this fashion, loading unit 70 is particularly suited to ensure that needle 14 is positively seated within jaws 4 and 5 of suturing apparatus 1 prior to removal of needle 14 from loading unit 70. This has the obvious advantages of ensuring needle 14 does not fall out of jaws 4 or 5 due to incomplete positioning or only partial securement therein.

Referring now to FIGS. 21 and 22, once jaws 4 and 5 have been fully closed about needle 14, end blade 16 or 29 is slid forward to firmly secure needle 14 within jaws 4 or 5, respectively. Suturing apparatus 1 may be lifted in the vertical direction causing elongate member 3 to pull free of tabs 86 and enabling jaws 4 and 5 to pass through gap 100, thereby allowing suturing apparatus 1 to be removed from loading unit 70. As needle 14 is pulled free of loading unit 70, suture 18 attached thereto is pulled through aperture 108 causing at least a portion of suture 18 to unravel from suture reel 120 as suture reel 120 rotates with respect to body portion 72. Reel guides 132 in conjunction with a male and female members 116 and 118, respectively, enable suture reel 120 to freely rotate and allow suture 18 to be withdrawn from loading unit 70. In this manner, loading unit 70 enables a user to rapidly and positively seat needle 14 within jaws 4 and 5 of a surgical suturing apparatus 1 while maintaining a suture 18 in a neat and secure condition until such time as needle 14 is pulled free of loading unit 70.

Loading unit 70 may be formed of any suitable material such as, for example, polycarbonate or other medical plastics. Suture reel 120 may also be formed of any similar suitable material. Additionally, various labeling methods may be employed to indicate the size and type of needle and suture loaded in unit 70 or the type of suturing apparatus to be used therewith.

Referring now to FIG. 23, there is disclosed another alternate embodiment of a loading unit suitable for use with a surgical suturing apparatus that is smaller, uses less material, and consequently is less costly to manufacture than loading unit 70. Loading unit 270 is provided to rapidly and positively seat a needle or surgical incision member and suture such as, for example needle 14 and suture 18 (not shown in FIG. 23), within the jaws of the surgical suturing apparatus.

Loading unit 270 generally includes a body portion 272 having a handle or finger tab 274 extending proximally therefrom. As used herein with reference to loading unit 270, the term "proximally" refers generally in the direction toward the holding hand of the user. Preferably finger tab 274 may include a plurality of ridges 276, or be otherwise textured, to enhance the gripping ability of the user.

Loading unit 270 is provided to support needle 14 in a manner to facilitate gripping or loading needle 14 into a surgical suturing instrument. Thus, loading unit 270 includes a needle support member 278 formed on body portion 272 to support or suspend needle 14 by a central portion thereof. Preferably support member 278 includes a pair of flexible fingers 280 which hold a central portion of needle 14. Apparatus receiving structure may be provided to guide jaws 4 and 5 adjacent support member 278. The apparatus receiving structure may include a pair of jaw support shelves 282 which are provided adjacent and below either the side of support member 278 to define a pair of recesses adjacent thereto. Shelves 282 further serve to align a pair of jaw members positioned thereon in a manner to grasp needle 14.

Additionally, the apparatus receiving structure may include various other alignment structure to guide or orient the jaws of a surgical suturing apparatus into position on loading unit 270 in order to grasp and remove needle 14. For example, an elongate member alignment structure 284 may be provided to guide a barrel housing or elongate portion of a suturing instrument into position on loading unit 270. Alignment structure 284 generally includes a pair of side tabs 286 which surround the suture apparatus elongate portion. Additionally, a support stud 288 (shown in phantom in FIG. 23) may be provided on a bottom edge of alignment structure 284 to maintain the elongate portion in proper vertical alignment with a corresponding recess in the suture apparatus elongate portion. Further, a recess such as for example, recess or cup 290, may be provided between jaw support shelves 282 to support the distal end of the elongate portion of a surgical suturing apparatus. When inserted in alignment structure 284, the distal end of the surgical suturing apparatus elongate portion will abut a distal end 292 of needle support member 278 to limit advancement of the jaws within the loading unit.

Various structure or safety features may be provided to ensure that needle 14 may not be removed from loading unit 270 until needle 14 has been firmly grasped by completely closing the surgical instrument suturing jaws. The safety mechanism 296 is provided to prevent lifting of the jaws, and thus lifting of needle 14 out of loading unit 270 before needle 14 has been firmly grasped by the jaws. Safety mechanism 296 generally includes a pair of blocking members 298 which are suspended above and adjacent either side of needle support member 278. Blocking members 298 prevent vertical movement of the jaws out of loading unit 272 until the jaws are closed, thereby firmly grasping needle 14. Additionally a ramped face 297 on support member 278 helps prevent premature longitudinal withdrawal of the jaws from loading unit 270. Once the jaws of a surgical suturing apparatus have been firmly and positively closed about needle 14, jaws may be lifted vertically through a gap 200 formed between members 298 in order to remove needle 14 from loading unit 270. Thus, members 298 in conjunction with ramped face 297 aid in ensuring that a needle 14 is not removed from the loading unit 270 until jaws have been fully closed and firmly grasp needle 14.

As noted hereinabove, needle 14 is preferably provided with a length of suture material 18. It is desirable to maintain the length of suture material 18 in a orderly and secure fashion until such time as needle 14 is removed from loading unit 70. Loading unit 270 includes a guide notch 202 which guides a length of suture into a hollow body cavity (not shown) of loading unit 270. In addition, slot 203 aids in ease of manufacture of the loading unit, by allowing easier insertion of the suture 18 into the unit 270. Suture 18 extends through an aperture 208 formed in a distal portion of finger tab 274 and extends into a hollow body cavity in the back of unit 270. Additionally, a channel 210 may be provided in body portion 272 to guide the length of suture between notch 202 and hollow body cavity 204. Thus, the length of suture 18 is neatly and securely stored within loading unit 270 prior to removal of needle 14.

The suturing apparatus is loaded using loading unit 270 substantially as described above and depicted in FIGS. 20–22. As described above, loading unit 270 has safety advantages similar to those of loading unit embodiment 70 to help prevent needle 14 from falling out of jaws 4 or 5 due to incomplete positioning or only partial securement therein.

Loading unit 270 and the accompanying suture reel located in the back of the unit may be formed of any suitable material such as, for example, polycarbonate or other medical plastics. Additionally, various labeling methods may be employed to indicate the size and type of needle and suture loaded in unit 270 or the type of suturing apparatus to be used therewith.

Regardless of the loading mechanism employed, once a new needle, suture and anchor are loaded into jaws 4 and 5, the lockout mechanism must then be re-armed, as described above, by pulling knobs 38 and 39 proximally so that plungers 36 and 37 re-engage surface 48 of housing 61. Wheel 23 must then be mined, placing blade 16 or 29 in a forward position so that it intersects needle 14, thereby retaining needle 14 when jaws 4 and 5 are opened, allowing the instrument to pierce another portion of tissue.

It will be understood that various modifications may be made to the embodiments disclosed herein. For example, the unit may be color coded to indicate the size and type of needle and suture found in the unit. Therefore, the above description should not be construed as limiting, but merely as exemplifications of preferred embodiments. Those skilled in the art will envision other modifications within the scope and spirit of the claims appended hereto.

The foregoing is considered illustrative only of the principles of the loading apparatus. Further, this is not intended to be limited to the exact structure, construction and operation shown and described. Accordingly, all suitable modifications and equivalents fall within the scope of the claims.

We claim:

1. A loading unit for loading a needle into at least one of a pair of jaws of a surgical suturing apparatus comprising:
    a body portion;
    a needle releasably supported in the body portion;
    wherein the body portion includes jaw receiving structure to receive at least one of the jaws of the suturing apparatus for loading the needle into at least one of the jaws.

2. The loading unit as recited in claim 1, wherein the jaw receiving structure includes at least one cavity for receiving a pair of jaws of the apparatus.

3. The loading unit as recited in claim 2, further comprising a mounting member for releasably holding the surgical needle transverse to the longitudinal axis of the loading unit.

4. The loading unit as recited in claim 3, further comprising alignment structure to align a tubular portion of the apparatus.

5. A loading unit for loading a suture into at least one of first and second jaws of a surgical suturing apparatus comprising:
    a body portion, the body potion including needle mounting structure configured to releasably mount a needle in the body portion and a cavity for receiving at least the first jaw such that movement of at least the first jaw within the cavity to a closed position enables the needle to be secured to the first jaw.

6. A loading unit as recited in claim 5, further comprising a surgical needle mounted within the mounting structure.

7. A loading unit as recited in claim 6, wherein the needle is mounted transverse to a longitudinal axis of the loading unit.

8. A loading unit as recited in claim 7, further comprising a suture connected to the surgical needle and releasably retained in the body portion.

* * * * *